(12) United States Patent
Neviere et al.

(10) Patent No.: US 9,329,113 B2
(45) Date of Patent: May 3, 2016

(54) MONITORING DEVICE FOR A VISCOELASTIC MATERIAL

(75) Inventors: Robert Neviere, Vert le Petit (FR); Guillaume Fouin, Montrouge (FR)

(73) Assignee: HERAKLES, Le Haillan (FR)

( * ) Notice: Subject to any disclaimer, the term of this patent is extended or adjusted under 35 U.S.C. 154(b) by 201 days.

(21) Appl. No.: 13/518,508

(22) PCT Filed: Dec. 13, 2010

(86) PCT No.: PCT/FR2010/052680
§ 371 (c)(1),
(2), (4) Date: Aug. 28, 2012

(87) PCT Pub. No.: WO2011/086254
PCT Pub. Date: Jul. 21, 2011

(65) Prior Publication Data
US 2012/0318065 A1    Dec. 20, 2012

(30) Foreign Application Priority Data

Dec. 23, 2009   (FR) ...................................... 09 59538

(51) Int. Cl.
*G01N 11/00* (2006.01)
*G01N 3/32* (2006.01)
*G01N 11/16* (2006.01)

(52) U.S. Cl.
CPC .................. *G01N 3/32* (2013.01); *G01N 11/16* (2013.01); *G01N 2203/0051* (2013.01); *G01N 2203/0094* (2013.01); *G01N 2203/0623* (2013.01)

(58) Field of Classification Search
CPC ....... G01N 11/00; G01N 11/02; G01N 11/04; G01N 11/162
USPC .......................................................... 73/54.01
See application file for complete search history.

(56) References Cited

U.S. PATENT DOCUMENTS

| 4,074,563 A | 2/1978 | Briar et al. |
| 4,706,199 A | 11/1987 | Gluerin |
| 5,038,295 A | 8/1991 | Husband et al. |
| 5,059,914 A * | 10/1991 | Lacombe et al. ............. 324/642 |
| 2005/0235741 A1 | 10/2005 | Covas et al. |

FOREIGN PATENT DOCUMENTS

| EP | 0130944 | 4/1985 |
| EP | 0317356 | 5/1989 |
| GB | 1247371 | 9/1971 |
| WO | WO 95/28629 | 10/1995 |

* cited by examiner

*Primary Examiner* — Daniel S Larkin
*Assistant Examiner* — Alex Devito
(74) *Attorney, Agent, or Firm* — Hamre, Schumann, Mueller & Larson, P.C.

(57) ABSTRACT

A device for monitoring a viscoelastic material by subjecting the sample to vibration and analyzing the response of the sample to such vibration. According to the invention, the sample (13) is placed in a chamber (20) situated between a vibration source (22) and a vibration sensor (25), these elements being pressed towards each other by means (35, 39) for applying initial mechanical loading.

16 Claims, 2 Drawing Sheets

Figure 2:
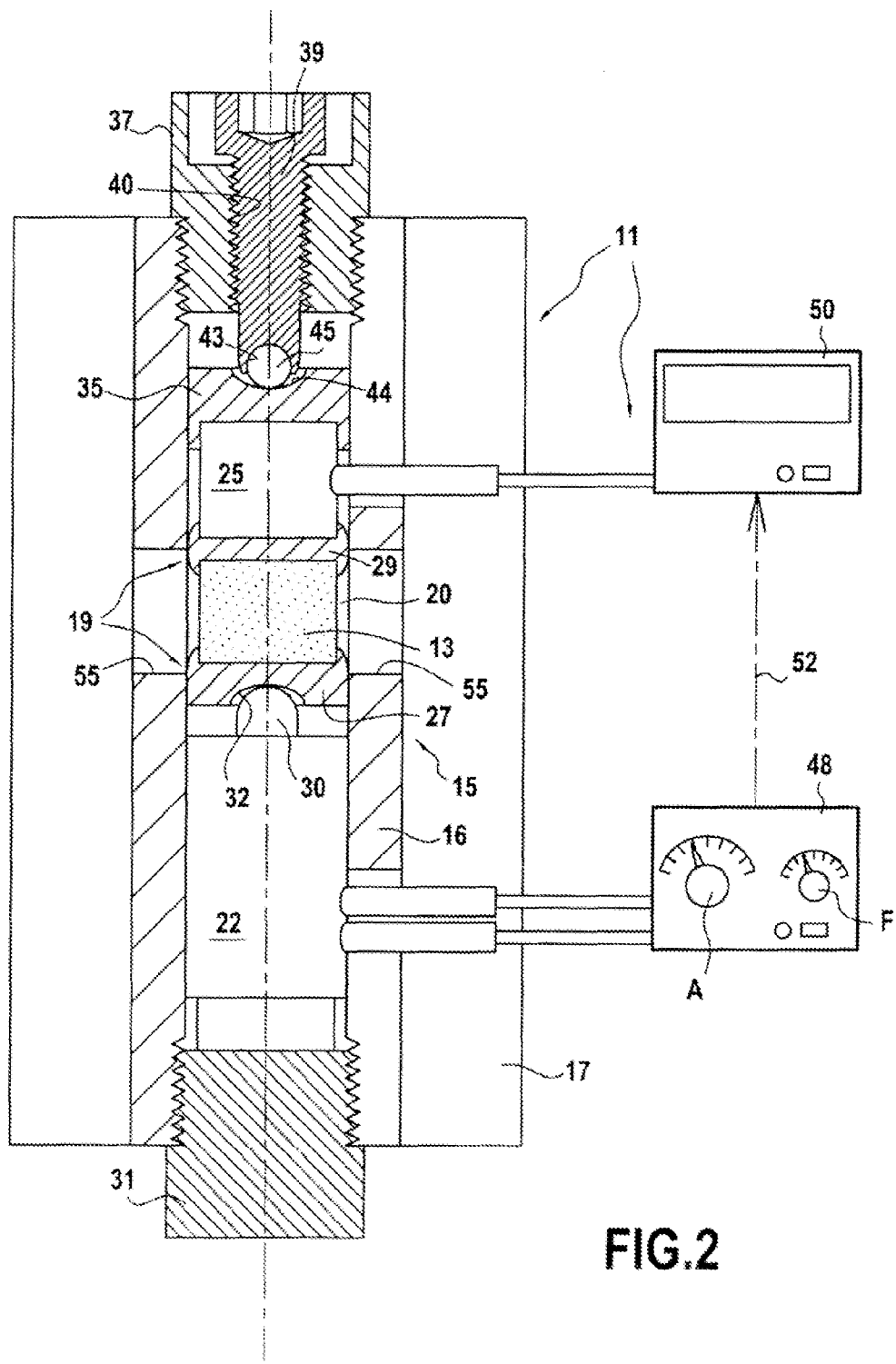

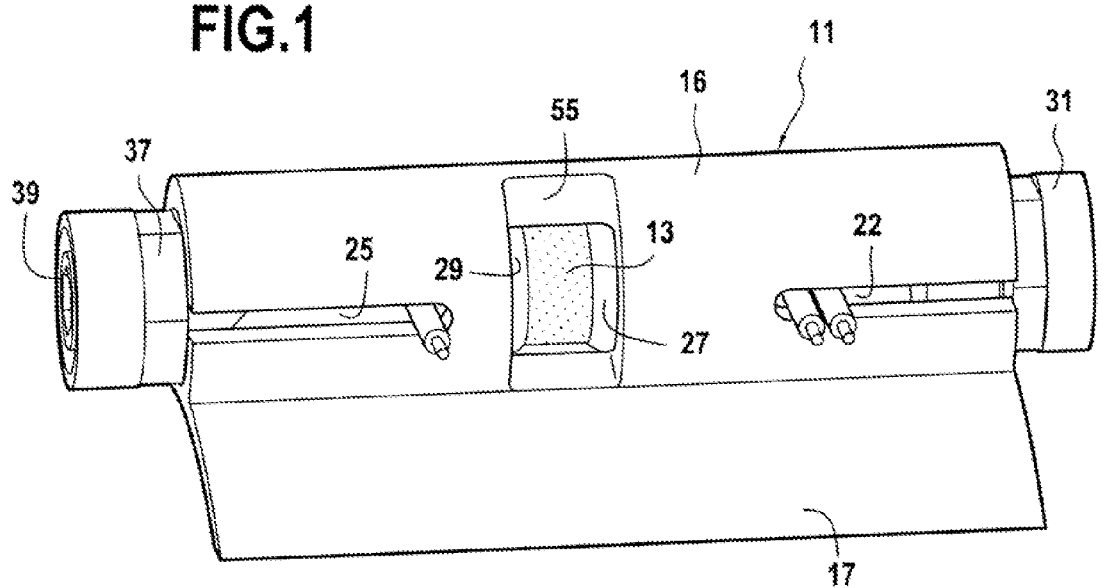
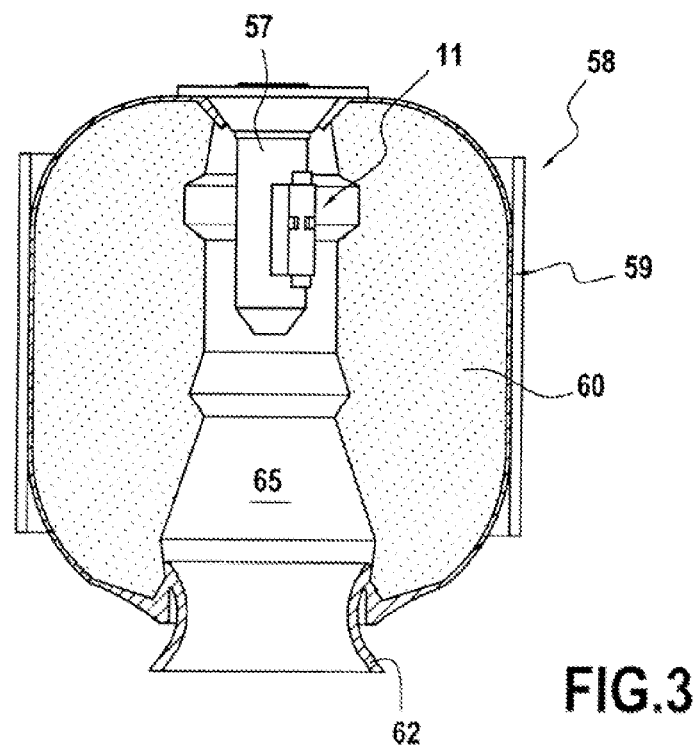

MONITORING DEVICE FOR A VISCOELASTIC MATERIAL

The invention relates to a device for monitoring a solid viscoelastic material such as an elastomer, a cross-linked polymer, or a resin. Such a device is intended in particular to evaluate the aging of said material by periodically subjecting it to cycles of loading and measurement. A preferred field of application of the invention is monitoring the aging of a solid propellant charge in a thruster.

By way of example, in the field of propulsion, the mechanical properties of solid propellant charges in a thruster can be the subject of aging. This may occur in particular as a result of The environment in which the thruster is stored, e.g. because of the presence of oxygen, moisture, salt, temperature, and because of variations therein. Thus, oxygen present inside a channel for charging solid propellant may lead to the binder being oxidized, thereby causing it to be excessively cross-linked and thus hardening the viscoelastic mass. In the presence of high humidity, a solid propellant presents, on the contrary, a tendency to soften. During storage, solid propellant charges may thus either soften or harden depending on the storage environment. Degradation in the mechanical properties of a solid propellant charge can lead to failure when firing the thruster. It is therefore desirable to measure the variation over time of mechanical properties of a solid propellant charge in order to be able to decide on the suitability of the thruster itself for being fired. The same type of problem naturally also occurs in the field of explosives for military warheads.

It is known to measure the mechanical properties of a viscoelastic material; such measurement is based on the dynamic mechanical response of the material while it is being subjected to vibratory mechanical loading.

One such known measurement consists in applying an oscillatory strain to the material for analysis, at a frequency that is off resonance. The resulting dynamic force that is transmitted by the sample is measured. The principles of linear viscoelasticity are applicable at low levels of deformation of the sample. Under such conditions, analyzing the phase and the modulus of the strain and force signals picked up in response makes it possible at various loading frequencies to determine two parameters known as the "dynamic modulus" and the "loss factor" that are representative of the aging of the material.

More particularly, if a sinusoidal loading is applied to the material at a frequency f, then during a dynamic mechanical measurement, the loading signal may be written:

$$\sigma(t) = \sigma_0 \cdot \sin(\omega t)$$

where:
$\sigma_0$ is the amplitude of the loading cycle;
$\omega = 2\pi f$ is the angular frequency in radians per second (rad/s); and
t is time.

The deformation response signal (measurement) of a viscoelastic material is written as follows:

$$\epsilon(t) = \epsilon_0 \cdot \sin(\omega t - \delta)$$

where:
the loss factor is the tangent of the angle $\delta$; and
the dynamic modulus is the ratio of the amplitude of the loading signal to the amplitude of the deformation response signal of the material.

A laboratory appliance called a viscoanalyzer is known that serves to obtain the mechanical dynamic response of a sample. Such an appliance generally comprises an electrodynamic generator for generating sinusoidal signals at programmable frequency and amplitude, an electrodynamic excitation pot comprising in particular a magnetic circuit and excitation coils, which pot is powered by the generator, a dynamic strain sensor that measures the amplitude of the loading applied to the sample, and a structure comprising a sample-carrier containing the sample for analysis. The sample is stuck to the sample-carrier and a dynamic force detection sensor picks up the loading signal transmitted by the sample.

Such an assembly is very rigid, and very heavy, weighing about 200 kilograms (kg).

Such equipment can therefore be used for monitoring the mechanical properties of a mass of viscoelastic solid material over time in order to determine its aging only by taking a sample from a series of samples of the same viscoelastic solid material, or by cutting a sample from the material that is being monitored, and by performing the measurement using a viscoanalyzer of the above-described type.

Attempts have also been made to determine the aging of such a mass of viscoelastic material by incorporating piezoelectric sensors therein, which sensors are connected to measurement units for the purpose of periodically measuring over time how their mechanical properties vary, where this is correlated with aging. Thus, patent documents U.S. Pat. Nos. 4,074,563 and 5,038,295 describe methods of measuring the mechanical properties of a solid propellant charge by means of piezoelectric sensors implanted in the mass of propellant. One of the problems associated with that type of monitoring is the difficulty of implanting sensors in the viscoelastic material at the time it is fabricated, e.g. when the solid propellant is cast into the thruster. Furthermore, the presence of such sensors in the viscoelastic material locally modifies the properties of the material and can lead to failure (e.g. as a result of cracking). Such sensors may also lead to safety problems, in particular as a result of local heating. Above all, the location of the sensors in the material itself does not make it possible to track variation in the properties of the "skin" of the mass of said material, where the skin zone is the zone that is the most exposed to aging because of surface exchanges between the surface zones of the material and the environment.

It is therefore desirable to have a device available that is suitable for measuring the mechanical properties of a viscoelastic material in order to evaluate its aging, where said device is suitable for being incorporated in systems that are confined or dangerous.

The invention makes it possible to achieve this object.

Firstly, the invention provides a device for monitoring a viscoelastic material, the device being characterized in that it comprises a sample-carrier in which there is defined a chamber for receiving a sample of said material, and in that the sample-carrier also includes a vibration source coupled to a wall of said chamber, a vibration sensor coupled to another wall of said chamber, and means for applying initial mechanical loading in order to press The two above-mentioned walls of said chamber against the sample, said vibration sensor being connected to calculation means in order to extract from the signal delivered by said sensor at least one parameter representative of the state of said sample.

The vibration source may be a piezoelectric actuator applying strains of up to 15 micrometers ($\mu$m) at frequencies of up to 500 hertz (Hz). It is servo-controlled in position by control electronics and by an incorporated deformation strain gauge. The vibration sensor operates in compression, or in traction/compression.

The sample is preferably mounted between the two above-mentioned walls of the chamber. The positioning of at least one of the walls is adjustable. As a result, the sample is not bonded, but is merely held with a small amount of compression between those two walls. Adjusting a threaded rod makes it possible to adjust the compression preloading that holds the sample in the sample-carrier. Blocking means enable this preloading to be stabilized. The electrical output from the vibration sensor is connected to the above-mentioned calculation means that determine the parameters that are representative of aging. Said parameters are stored on each measurement and the way their values vary over time serves to assess said aging.

Surprisingly, it has been found that a small amount of loading applied initially to the sample suffices to keep it in place and to obtain a measurement that is reliable. A small amount of loading is used to mean a loading of less than 10 newtons (N) for example. It may advantageously be less than or equal to 5 N. A possible small reduction in the loading associated with the sample relaxing over time has no significant influence on the mechanical properties (modulus and loss angle) of the sample as measured. Consequently, these mechanical properties may be measured periodically without re-calibrating the preloading to its original value, and thus without taking action on the device. The device may therefore be implanted in a location that is relatively inaccessible, and in particular in the immediate proximity of a greater mass of the same viscoelastic material for which it is desired to monitor aging. Furthermore, the sample chamber defined by the two above-mentioned walls is provided with windows enabling the sample to make contact with the outside environment of the mass being monitored. Thus, said sample is subjected to the same aging conditions as the mass of viscoelastic material for which it is desired to monitor the aging.

The invention is particularly adapted to evaluating the aging of a solid propellant.

The invention can be better understood and other advantages appear more clearly in the light of the following description of a device in accordance with the principle of the invention, given purely by way of example and made with reference to the accompanying drawings, in which:

FIGS. 1 and 2 are schematic views of a device for monitoring solid viscoelastic material, in accordance with the invention; and FIG. 3 schematically illustrates the solid propellant charge of a thruster with the FIG. 1 device implanted therein.

With reference more particularly to FIGS. 1 and 2, there can be seen a device 11 for monitoring a viscoelastic material, which device is suitable for receiving a sample 13 of such a material, and here is in the form of a small cylindrical box. The device comprises a unit 15 comprising a generally cylindrical and tubular body 16 having a curved member 17 attached thereto enabling it to be fastened to a selected support in the vicinity of a larger mass of the same material, in a configuration as described below.

The body 16 constitutes a sample-carrier portion 19 since it has two walls 27 and 29 defining a middle chamber 20 therein for receiving the sample 13. On opposite sides of said chamber 20, the body houses a vibration source 22 in the form of a piezoelectric actuator, and a vibration sensor 25 (force sensor). The vibration source 22 is coupled to the wall 27 of the chamber, while the sensor 25 is coupled to another wall 29 of the same chamber. These two disk-shaped walls 27 and 29 clamp the sample between them and constitute two opposite parallel end walls of the chamber 20. They are not fastened inside the tubular body 16, but rather they are pressed with little loading against the two opposite faces of the sample 13.

By means of an axial projection 30, the vibration source 22 presses against the center of the facing face of the wall 27, which face includes a depression 32 in which the projection 30 is engaged. A screw 31 is engaged in a threaded end portion of the body 16. The vibration source 22 may bear against this screw, thereby defining the position of said vibration source inside the body.

The vibration sensor 25 is in contact with the wall 29 via one end and also with a kind of piston 35 that is slidably mounted in the body 16. The piston forms part of means for applying the initial mechanical loading on the sample 13 (which means are adjusted once and forever). More precisely, these load-applying means comprise a hollow-headed screw 37 engaged in another threaded end portion of the body 16 remote from its first end portion, and an adjustment screw 39 engaged in a threaded axial hole 40 in the screw 37.

The outside end of the adjustment screw 39 includes a hexagonal socket for adjustment purposes, and its inside end has a depression 43 facing a depression 44 formed in the middle of the piston 35. A ball 45 is interposed between these two depressions.

The vibration source 22 is fed with electrical energy by a sinewave voltage generator 48 of adjustable amplitude (A) and frequency (F). The vibration sensor is connected to a measurement and calculation device 50 receiving the sinusoidal vibratory signal delivered by the sensor. The measurement and calculation device 50 is designed to respond to the received signal by deducing the two above-defined parameters (loss factor and dynamic modulus), taking account of the excitation signal as transmitted by the generator 48 (connection 52). The design of the device 50 is within the competence of the person skilled in the art.

When the sample is in place, the initial loading of a few newtons is applied to the sample 13 via the walls 27 and 29 by adjusting the screw 39. This low initial loading serves to provide good coupling between the vibration source 22, the sample 13, and the sensor 25, without giving rise, over time, to significant relaxation of the material constituting the sample, thereby avoiding any need to periodically readjust the settings.

According to another advantageous characteristic, the chamber 20 has windows 55 putting the sample into contact with the outside environment in which the sample-carrier is installed. More precisely, the windows 55 are formed in the body 16, between the two walls 27 and 29 of said chamber.

FIG. 3 shows the above-described device implanted in a thruster 58 containing a charge of solid propellant. The sample-carrier is shaped and dimensioned so as to be placed in the vicinity of a mass of material of the same kind as that which is placed in said chamber. In other words, the sample 13 in this example is constituted by the same material as the material that constitutes the solid propellant charge 60.

In this example, the device is fastened by the curved member 17 along the ignitor 57 of the thruster 58. This comprises a body 59 extended by a nozzle 62 and housing the solid propellant charge 60. In its initial state, the charge includes an axial recess 65 communicating with the nozzle and housing the ignitor 57 and the device 11 of the invention. Prior to ignition, the sample is thus exposed to the same environmental conditions as is the charge 60 for which it is desired to evaluate aging.

During this period, the sample-carrier is permanently mounted inside the charge, but the generator 48 and the measurement and calculation device 50 are connected only during measurement stages.

Cycles of measuring the two above-mentioned parameters are performed periodically by connecting the generator 48 and the device 50. The measurements and/or the two calculated parameters are stored in order to be able to deduce how aging progresses therefrom.

The field of application of the invention is broader than that of the above example.

The viscoelastic materials in question may either Merely be in storage, or else they may be incorporated for functional purposes in other systems (cars, airplane, thruster, building, . . . ). Given the independent nature of the device, it is particularly suitable for use in systems that are isolated, confined, or dangerous, such as thrusters, warheads, nuclear power stations, space stations, undersea platforms.

The invention claimed is:

1. A device for monitoring aging of a viscoelastic material, comprising:
    a sample-carrier having a chamber for receiving a sample of said viscoelastic material, wherein the sample-carrier is shaped and dimensioned so as to be placed in a vicinity of a mass of material of the same kind as said sample which is placed in said chamber, said chamber is provided with one or more windows for putting said sample into contact with the same environment as the mass of material;
    a vibration source in the form of a piezoelectric actuator, coupled to a wall of said chamber;
    a vibration sensor configured to measure compression or traction/compression coupled to another wall of said chamber, the vibration sensor being configured to be connectable to a calculation device for determining at least one parameter representative of an aging state of the sample from a signal communicated by said vibration sensor; and
    load-applying means for applying initial mechanical loading in order to press the two above-mentioned walls of said chamber against the sample.

2. The device according to claim 1, wherein the load-applying means is configured to apply the initial mechanical loading of less than 10 N.

3. The device according to claim 2, wherein the load-applying means is configured to apply the initial mechanical loading of less than or equal to 5 N.

4. The device according to claim 1, wherein said vibration source emits a sinusoidal vibration at an adjustable frequency.

5. The device according to claim 4, wherein the at least one parameter is a loss factor of said viscoelastic material of said sample.

6. The device according to claim 4, wherein the at least one parameter is a dynamic modulus of said viscoelastic material of said sample.

7. The device according to claim 1, wherein said sample chamber is defined by the two above-mentioned walls arranged parallel to each other, and the portion of the chamber extending between said two walls includes said one or more windows.

8. The device according to claim 1, further comprising said sample of said viscoelastic material in said chamber, wherein said viscoelastic material is a solid propellant.

9. The device according to claim 1, further comprising the calculation device connected to the vibration sensor for receiving the signal from the vibration sensor and determining the at least one parameter from the signal.

10. The device according to claim 1, further comprising said sample of said viscoelastic material in said chamber, wherein said viscoelastic material is a solid material.

11. An assembly, comprising:
    a mass of solid viscoelastic material; and
    a monitoring device placed in a vicinity of the mass, the monitoring device comprising:
        a sample-carrier having a chamber containing a sample of the solid viscoelastic material, wherein the sample-carrier is shaped and dimensioned so as to be placed in a vicinity of a mass of material of the same kind as the sample in the chamber, and the chamber includes one or more windows configured for placing the sample into contact with the same environment as the mass of material,
        a vibration source in the form of a piezoelectric actuator coupled to a first wall of the chamber,
        a vibration sensor configured to measure compression or traction/compression coupled to a second wall of the chamber,
        a calculation device connected to the vibration sensor to transform a signal from the vibration sensor to at least one parameter representative of an aging state of the sample, and
        load-applying means configured to apply an initial mechanical load to press the first wall and the second wall against the sample.

12. The assembly according to claim 11, wherein the viscoelastic material is a solid propellant.

13. A process of monitoring aging of a mass of viscoelastic material, comprising the steps of:
    providing a mass of a viscoelastic material to be monitored;
    placing a sample of the viscoelastic material in a chamber of a sample-carrier disposed in a vicinity of the mass, the chamber being configured so that the sample is put into contact with the same environment as the mass;
    applying an initial mechanical loading to the sample by pressing two opposite walls of the chamber against the sample;
    loading the sample by actuating a piezoelectric actuator coupled to a first wall of the chamber, thereby vibrating the first wall of the chamber;
    measuring a response with a vibration sensor measure compression or traction/compression coupled to a second wall of the chamber; and
    extracting from the signal delivered by the vibration sensor at least one parameter representative of an aging state of the sample.

14. The process as in claim 13, comprising periodically subjecting the sample to cycles of loading and measurement.

15. The process as in claim 13, wherein the initial applied loading is less than 10 N.

16. The process as in claim 13, wherein the initial applied loading is less than or equal to 5 N.

* * * * *